Nov. 12, 1974 G. A. DELBARD Plant Pat. 3,647
ROSE PLANT
Filed Dec. 6 1973
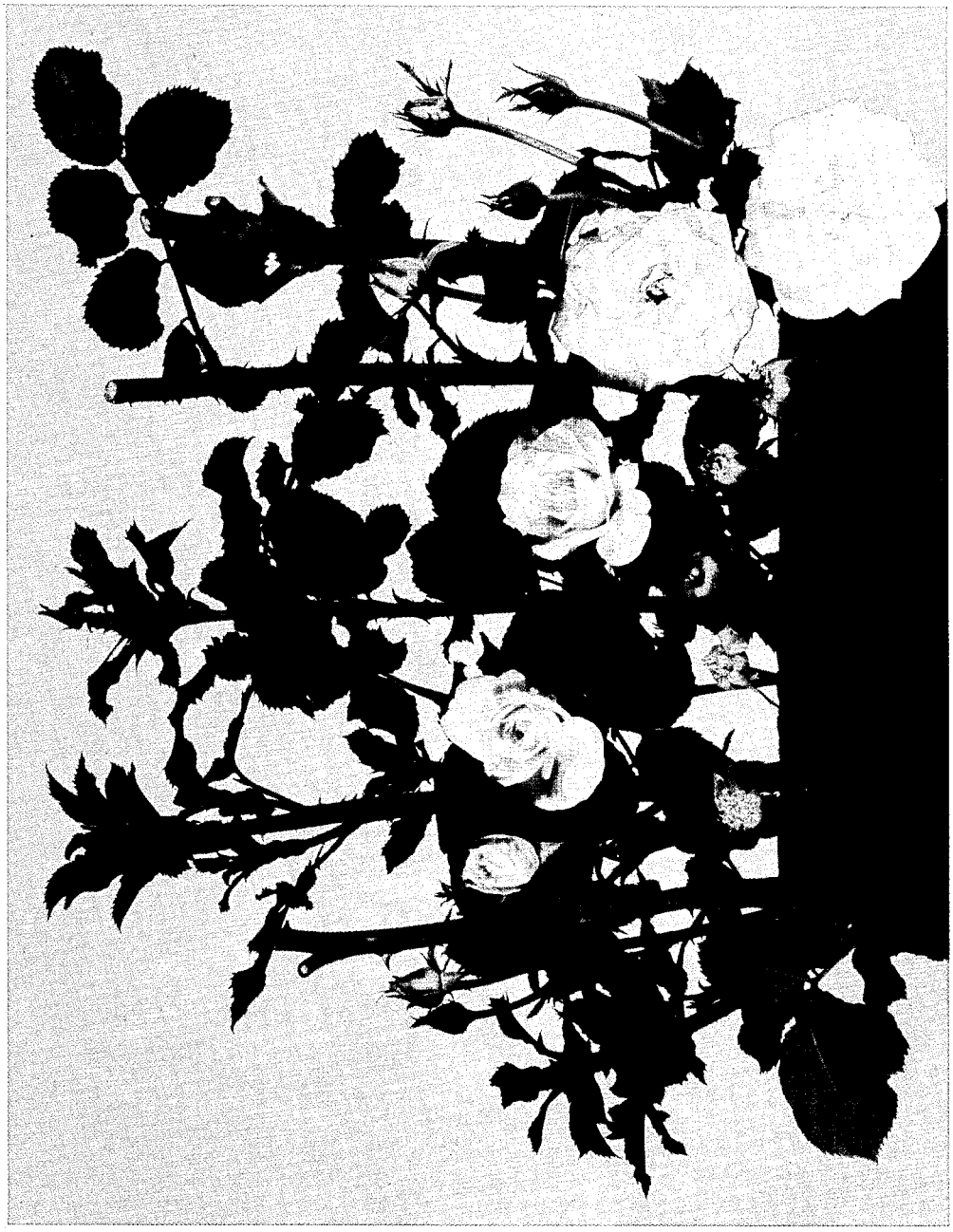

United States Patent Office

Plant Pat. 3,647
Patented Nov. 12, 1974

3,647
ROSE PLANT

Georges Alphonse Delbard, Paris, France, assignor to The Conard-Pyle Company, West Grove, Pa.

Filed Dec. 6, 1973, Ser. No. 422,147
Int. Cl. A01h 5/00
U.S. Cl. Plt.—25 1 Claim

ABSTRACT OF THE DISCLOSURE

A new and distinct variety of rose plant of the Floribunda class which was originated by me by crossing the variety Zambra (Plant Patent No. 2,140) with an unnamed seedling whose parentage was [(Orleans Rose × Goldilocks, Plant Patent No. 672)] × (Unnamed seedling of Orange Triumph × Floradora).

SUMMARY OF THE INVENTION

My present invention relates to a new and distinct variety of rose plant of the Floribunda class which was originated by me by crossing the variety Zambra (Plant Patent No. 2,140) with an unnamed seedling whose parentage was also an unnamed seedling of Orleans Rose (unpatented) × Goldilocks (Plant Patent No. 672 crossed with an unnamed seedling of Orange Triumph (unpatented) and Floradora (unpatented): Zambra (Plant Patent No. 2,140) × [(Orleans Rose × Goldilocks) × (Orange Triumph seedling × Floradora)].

My objective in making these crosses was to produce a new and improved rose variety of vigorous yet compact growth habit, free and continuous flowering, superior weather tolerance, combined with a distinctive color different from all other varieties. I was successful in my objective as evidenced by the following combination of characteristics which are outstanding in my new rose:

1. A plant of unusual vigor and freely branched;
2. Compact, even growth habit of spreading form making a rounded bush as broad as it is high;
3. Flowers produced freely over the plant and continuously through the season;
4. An attractive bud opening with petals slightly cupped, of semi-doubleform maturing with the petals loosely rolled outward;
5. An attractive, distinctive pink color with shadings of yellow and red to give an overall coral effect;
6. Flowers occurring in clusters often of ten or more;
7. Abundant foliage covering the plant completely and having above average resistance to common garden rose diseases; and
8. Greater tolerance to extremes of winter and summer weather than the average for the Floribunda class.

When compared to its seed parent, my rose has more pink in the flower color and with less change of color during the life of the flower and has a more compact habit of growth with greater vigor and is more floriferous.

The unnamed seedling which was the pollen parent of my new rose had no commercial value but had merit for breeding because of its vigorous, compact growth, abundant foliage which was successfully transmitted to my new rose.

Asexual reproduction of my new rose by budding at West Grove, Pa., and Malicorne, France, showed that its characteristics and distinction come true to form and are established and transmitted through succeeding propagations.

BRIEF DESCRIPTION OF DRAWING

The accompanying drawing shows as nearly true as is reasonably possible to make the same in a color illustration of this character, typical specimens of the flowers and foliage.

DETAILED DESCRIPTION OF DISCLOSURE

The following is a detailed description of my new variety with color terminology in accordance with the color chart of the Royal Horticultural Society.

Type: Hardy; bush; for garden decoration.
Class: Floribunda.
Propagation: It does hold its distinguishing characteristics through succeeding propagations by cuttings and budding.

FLOWER

Locality Where Grown: West Grove, Pa.
Flowers Borne: Singly, several to stem; in irregular, flat cluster; on normal, medium long stems.
Quantity of Bloom: Abundant, outdoors.
Continuity: Continuous.
Fragrance: Slight; tea.
Bud: Peduncle: Short, medium length; slender; medium erect; light side 194B, dark side 178B, some on both sides 194B; almost smooth; few hairs; green.

*Before calyx breaks.*—Size: Small. Form: Pointed; with foliaceous appendages on the surface of the bud; with slender, medium cut foliaceous parts extending beyond the tip of the bud equal to ¾ or more of its length.

*As calyx breaks.*—Color: 35B.

*As first petal opens.*—Size: Small. Form: Long, pointed. Color: Outside: 35B flushed with 35C. Inside: 35A with 34B on lower part of petal with small crescent of 11B at point of attachment. Opening: It does open up well.

Bloom: Size when fully open: Medium, 2¼ inches to 2½ inches.

*Petalage.*—Double, but the stamens not hidden; from 17 to 21 petals; arranged regularly.

*Form.*—Flat, open at first; becoming flat, open; petals remaining at first rolled outward; becoming later at maturity loosely flat, rolled outward.

Petals: Thin; soft; with inside satiny; outside satiny.

*Shape.*—Outer: Round. Intermediate: Round. Inner: Obovate.

*Color.*—Colors may be modified by being shaded with other colors.

This description of a newly opened flower was made from a rose grown outdoors in August 1973 at West Grove, Pa.

*Color.*—Outer petal: Outside surface—Lower part of petal 35D blending into upper part to 35C. Inside surface—35B; crescent shape base 11B at point of attachment. Intermediate petal: Outside surface—35C with base 11B. Inside surface—35A with crescent shape base of 11A at point of attachment. Inner petal: Outside surface—35B with base 11B. Inside surface—35A with base 11A at point of attachment.

This description was made from a rose that was open for three days outdoors in August, 1973, at West Grove, Pa.

*Color.*—Outer petal: Outside surface—Base 36D, top of petal 35D striped upward from base with 36D. Inside surface—Base 36C blending into 35B at upper part of the petal. Margin of petal 33A. Inner petal: Outside surface—Base 36C blending into 35C at upper part of the petal. Inside surface—Base 36B blending into 35B on upper ¾ of petal.

*General color effect.*—Newly opened flower: 40D. Three days open: 41D.

*Behavior.*—Persist; fading pink.

*Flower longevity.*—In the garden three days in August; cut roses grown outdoors kept at living room temperatures 4 days in August.

Reproductive Organs:

*Stamens.*—Medium number; arranged regularly about pistils.

*Filaments.*—Most with anthers; medium length. Color: Newly opened 13A, mature 13B.

*Anthers.*—Open at various times; small size. Color: Newly opened 13B turning in mature flower to 166A. Occasionally an anther fused with a petaloid.

*Pollen.*—No pollen observed.

*Pistils.*—Few.

*Styles.*—Uneven; medium length; thin; bunched columnar.

*Stigma.*—Yellow.

*Ovaries.*—Some protruding from receptacle.

*Hips.*—None observed.

*Sepals.*—None observed.

*Seeds.*—Peduncle dies and drops off.

PLANT

Foliage: Leaves: 3, 5, 7 leaflets; abundant; medium size; soft.

*Leaflets.*—Shape: Ovoid with apex acute, base round, serrate.

*Color.*—Mature—Upper surface: 136A. Under surface: 136C. Young—Upper surface: 183A. Under surface: 183A.

*Rachis.*—Medium—Upper side: Smooth, grooved. Under side: Sparsely prickly.

*Stipules.*—Moderately long; medium wide; short points; turning out at an angle of more than 45°.

*Disease.*—Resistance comparable to the average variety growing under the same cultural conditions.

Growth:

*Habit.*—Bushy, much branched.

*Growth.*—Free.

*Canes.*—Medium.

*Maint stems.*—Dull. Color: 139B.

*Prickles.*—Several. Color: 147C, old prickles 166A.

*Hairs.*—None.

*Branches.*—Dull. Color: 147A.

*Prickles.*—Many. Color: Young 147C, other 166A.

*Hairs.*—None.

*New Shoots.*—Dull. Color: 139B.

*Prickles.*—Several. Color: 182B.

*Hairs.*—None.

I claim:

1. A new and distinct variety of rose plant typical of the class known as Floribunda substantially as herein disclosed, characterized as to novelty by a unique combination of vigorous, freely branched and compact growth habit, giving the plant rounded form and covered with abundant foliage of medium green color and showing resistance to common rose diseases, with greater tolerance to seasonal temperature variations than the average for the class; bearing an abundance of flowers, usually in clusters, continuously through the season, these flowers being semi-double with attractive form and of distinctive pink color with shadings of yellow and red giving an overall coral effect.

No references cited.

ROBERT E. BAGWILL, Primary Examiner